United States Patent
Yan et al.

(10) Patent No.: US 11,932,869 B2
(45) Date of Patent: Mar. 19, 2024

(54) METHOD FOR DIGESTION OF RPE CELLS

(71) Applicant: EYECURE THERAPEUTICS, INC. (JIANGSU), Wuxi (CN)

(72) Inventors: Zhanhai Yan, Wuxi (CN); Lei Xie, Wuxi (CN)

(73) Assignee: EYECURE THERAPEUTICS, INC. (JIANGSU), Wuxi (CN)

(*) Notice: Subject to any disclaimer, the term of this patent is extended or adjusted under 35 U.S.C. 154(b) by 478 days.

(21) Appl. No.: 16/958,119

(22) PCT Filed: Feb. 20, 2019

(86) PCT No.: PCT/CN2019/075533
§ 371 (c)(1),
(2) Date: Jun. 25, 2020

(87) PCT Pub. No.: WO2019/129306
PCT Pub. Date: Jul. 4, 2019

(65) Prior Publication Data
US 2020/0362304 A1    Nov. 19, 2020

(30) Foreign Application Priority Data
Dec. 26, 2017 (CN) .......................... 201711430944.2

(51) Int. Cl.
*C12N 5/079* (2010.01)
*C12N 9/50* (2006.01)

(52) U.S. Cl.
CPC .............. *C12N 5/0621* (2013.01); *C12N 9/50* (2013.01); *C12N 2509/00* (2013.01)

(58) Field of Classification Search
CPC ............................... C12N 5/0621; C12N 9/50
See application file for complete search history.

(56) References Cited

U.S. PATENT DOCUMENTS

| | | | |
|---|---|---|---|
| 2013/0224156 A1 | 8/2013 | Takahashi et al. | |
| 2020/0239842 A1* | 7/2020 | Zhong | C12N 5/0621 |

FOREIGN PATENT DOCUMENTS

| | | |
|---|---|---|
| CN | 102939100 A | 2/2013 |
| CN | 104312976 A | 1/2015 |
| CN | 106282096 A | 1/2017 |
| CN | 106434531 A | 2/2017 |
| CN | 108728413 A | 11/2018 |
| WO | 2015087231 A1 | 6/2015 |
| WO | 2016108239 A1 | 7/2016 |
| WO | WO-2017017686 A1 | 2/2017 |

OTHER PUBLICATIONS

SAFC Biosciences Product Information Dulbecco's Phosphate Buffered Salin, 2006, 2 pages. See <chrome-extension://efaidnbmnnnibpcajpcglclefindmkaj/https://www.sigmaaldrich.com/deepweb/assets/sigmaaldrich/product/documents535/539/p56064.pdf> Retrieved on May 10, 2023.*
International Preliminary Report on Patentability for International Patent Application No. PCT/CN2009/075533, dated Apr. 8, 2020 (16 pages).
International Search Report for International Patent Application No. PCT/CN2019/075533, dated May 20, 2019 (10 pages).
Stasi et al., "Optimal Isolation and Xeno-Free Culture Conditions for Limbal Stem Cell Function," IOVS 55:375-386 (2014).
Li et al. "Activin A promotes human embryonic stem cells to directly differentiate into retinal pigment epithelium cells." Chin Sci Bull. 2016, 61:1816-21. [English abstract on p. 1821].
Edmondson et al. "Three-dimensional cell culture systems and their applications in drug discovery and cell-based biosensors." Assay Drug Dev Technol. 2014, 12(4):207-18.

* cited by examiner

*Primary Examiner* — Suzanne M Noakes

(74) *Attorney, Agent, or Firm* — Goodwin Procter LLP

(57) ABSTRACT

The present invention disclose a method for digesting RPE cells to dissociate adherent cells, comprising steps: (1) using 1× recombinant enzyme TrypLE to cover RpE cells evenly; (2) using neutral protease Dispase II solution to cover RPE cells evenly, in which steps (1) and (2) are applied step by step.

10 Claims, 5 Drawing Sheets

METHOD FOR DIGESTION OF RPE CELLS

This application is a U.S. National Stage Application of International Patent Application No. PCT/CN2019/075533, filed Feb. 20, 2019, which claims the benefit of Chinese Patent Application serial number 201711430944.2, filed Dec. 26, 2017, the contents of each of which are hereby incorporated by reference in their entirety.

TECHNICAL FIELD

The present invention generally relates to the field of life science, and specifically to a method for digesting RPE cells to dissociate adherent cells.

TECHNICAL BACKGROUND

Retinal pigment epithelium (abbreviated as RPE) cells constitute of monolayered pigment epithelium cell, in a very regular alignment. The cells are polygonal and consist of into three parts: the top part, body part and basilar part. The RPEs are continuous monolayered cells located outside of the retina, and is named for sieve-like morphology and enriched cytosolic melanin, which play important roles in maintenance and self-renewal of retinal cells, such as phagocytosis and digestion of OS from shed photoreceptor cells; promoting regeneration of 11-cis retinaldehyde, an important media in optic circulation; regulate intraocular immune response; participating in the formation of retinal vascular barrier, etc.

Senile macular degeneration is also known as age-related macular degeneration (AMD). Most cases started at the age of 50 and the prevalence becomes higher with age increment. There is no significant relationship between the incidence and gender or race. In AMD, both eyes suffer simultaneously or sequentially. The main symptoms and diagnosis of AMD are loss of central visual, dark shadow occlusion in the central visual field, and deformation of visual objects. As the cause of the disease is still unclear, there is no effective treatment or fundamental precautions against AMD. AMD is mainly characterized by decreased capability of retinal pigment epithelium cells in phagocytosis and digestion of the rod outer segment, which resulted in retention of the residual bodies from the incompletely digested membrane in the basal cell plasm, expelling them out of the cell, and depositing on Bruch membrane, and the formation of drusen. There are two types of AMD: dry and wet. Dry AMD is more common. It is a disease of choroidal capillary and photoreceptor deficiency caused by RPE progressive malnutrition. The typical feature of wet AMD is the formation of choroidal neovascularization (CNV), which results in severe visual loss. Other than cell replacement therapy, there is currently no effective way to reverse such a degenerative process and restore a vision.

Trial of RPE cell treatment for AMD shows that the transplantation of normal RPE cells in the subretinal cavity can delay the progressive loss of visual function. The trial of RPE cell transplantation in RPE genetic defect animal model and AMD patients shows that it can delay the degeneration of retina and improve visual function. Therefore, RPE cells are expected to become stem cell drug in the near future. However, due to the particularity of RPE cells, they need to overcome two major challenges in the production process to become stem cell drug, one of which is the method of dissociating adherent RPE cells. The method in present disclosure aims to address this problem.

SUMMARY OF THE INVENTION

In one respect, the present invention discloses a digestive enzyme composition, comprising a recombinant enzyme TrypLE™ (recombinant trypsin-like enzyme) and a neutral protease Dispase II, which can be used to dissociate adherent RPE cells.

In one embodiment, the recombinant enzyme TrypLE™ is preferably 1×TrypLE™ Select.

In another embodiment, the neutral protease Dispase II is selected from any of the concentrations from 0.5 mg/mL to 4.0 mg/mL, more preferably 2.0 mg/mL.

In another respect, the present invention discloses the use of a digestive enzyme composition in preparation of a reagent or kit for dissociating adherent RPE cells, in which the digestive enzyme composition comprises the recombinant enzyme TrypLE™ and the neutral protease Dispase II.

In another respect, the present invention also discloses the use of a digestive enzyme composition in dissociating adherent RPE cells, in which the digestive enzyme composition comprises the recombinant enzyme TrypLE™ and the neutral protease Dispase II.

In one embodiment, the neutral protease Dispase II is selected from any of the concentrations from 0.5 mg/mL to 4.0 mg/mL, more preferably 2.0 mg/mL.

In another respect, the present invention also discloses a method for digesting RPE cells to dissociate adherent RPE cells, comprising steps:

(1) using 1× recombinant enzyme TrypLE™ to cover RPE cells evenly; and (2) using neutral protease Dispase II solution to cover RPE cells evenly; wherein, steps (1) and (2) can be applied step by step.

Wherein, the neutral protease Dispase II is selected from any of the concentrations from 0.5 mg/mL to 4.0 mg/mL, more preferably 2.0 mg/mL.

In one specific embodiment, the RPE cells are cells cultured for any of the time points from 15 to 17 days.

In one specific embodiment, the condition for treating RPE cells by the recombinant enzyme TrypLE™ in the step (1) is incubation for 14 to 16 minutes at 37° C.

In one specific embodiment, the condition for treating RPE cells by the neutral protease Dispase II in the step (2) is incubation for 10 to 15 minutes at 37° C.

In any of the aforementioned methods, the steps also comprise: washing the cells with calcium and magnesium free DPBS and discarding the wash buffer before the step (1) or (2).

In one specific embodiment, the DPBS or recombinant enzyme TrypLE™ used in the invention need to be pre-heated in water bath at 37° C. for 5 to 10 minutes before using.

In one specific embodiment, discarding the neutral protease Dispase II solution after digestion, aspirating the cells by gently pipetting, collecting the cells, adding RPE complete medium, centrifuging at 2000 rpm for 5 minutes and discarding the supernatant.

In one specific embodiment, the RPE cell is cultured in T25 flask.

In one specific embodiment, the neutral protease Dispase II solution is prepared as follows: extracting the neutral protease Dispase II stock-solution at −20° C., with the concentration of 40 mg/mL; Adding DPBS (calcium and magnesium free) into the stock-solution after thawing to prepare neutral protease Dispase II solution with proper concentration. The recommended concentration of neutral protease Dispase II solution is 2.0-4.0 mg/mL, i.e. the enzyme activity is 1.5-2.4 IU/mL.

In present invention, RPE cells may be RPE cells of various culture generations isolated and purified from any of the ocular tissue, preferably P2 generation.

Beneficial Effects

To provide a simple and easy-to-use method to dissociate adherent RPE cells, which provides a strong support for culturing, expansion and purification of RPE cells in vitro, and provides a new source for treating RPE injury diseases such as AMD; the specific advantages are as follows:
1. The recombinant enzyme TrypLE™ is milder than trypsin, and more controllable for the process;
2. The cell adherent ratio after cryopreservation in recombinant enzyme TrypLE™+neutral protease Dispase II group is significantly higher than that of the trypsin+neutral protease Dispase II group, and has the synergistic effect, which is much better than that of TrypLE™, trypsin or neutral protease Dispase II alone.
3. recombinant enzyme TrypLE™+neutral protease Dispase is safer as digestive solution without animal origin.

DETAILED DESCRIPTION

The present invention will be further illustrated in detail below with reference to the specific examples. These examples are only used to describe the invention, and shall not be construed as limiting the scope or content of the invention in any way.

Unless defined otherwise, all technical and scientific terms used herein have the same meaning as commonly understood by one of ordinary skill in the art to which the invention pertains.

As described herein, terms "TrypLE™", "recombinant enzyme TrypLE™", and "Tryple" are interchangeable.

As described herein, terms "Dispase II", "neutral protease II", and "disperse enzyme II" are interchangeable, and refers to a non-specific matrix metalloproteinase.

As described herein, term "adherent rate" refers to the percentage of adherent and survival cells after digestion, freeze-thaw, recovery centrifugation of the same number of cells, and plate culture of the same number of cells after centrifugation precipitation. Therefore, the adherent rate used in the invention reflects the cell viability after cryo-preservation. Recovery rate is the ratio of the count value of the recovered cells after washing to that of before cryo-preservation.

EXAMPLES

Example 1: Study of Digestive Solution on the Cell of P2 Generation

Figure 1:
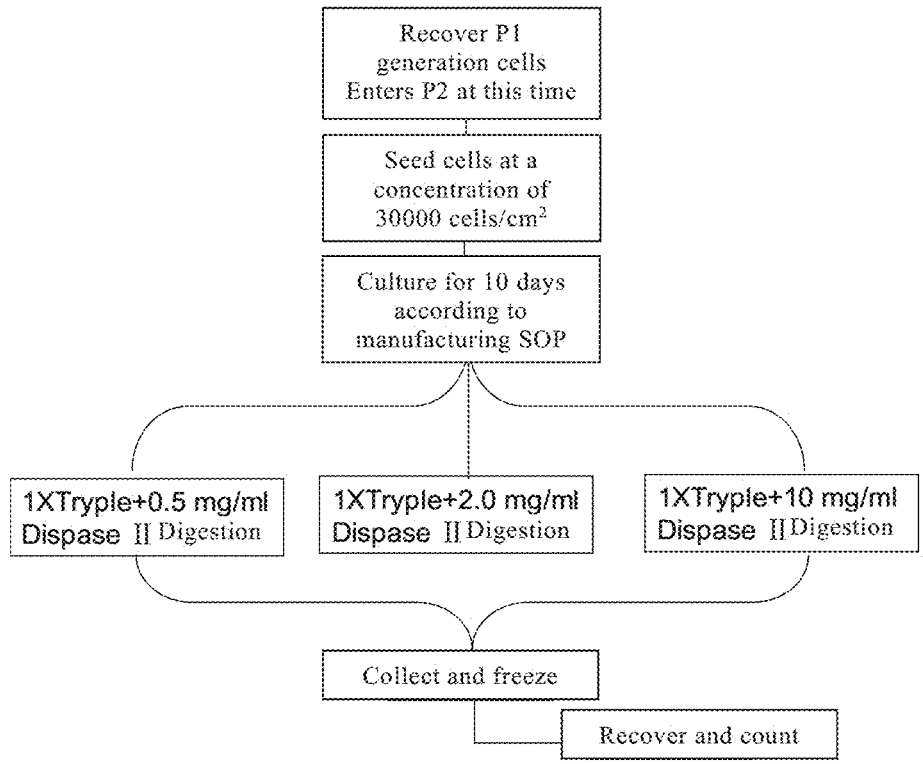
FIG. 1 shows the experimental flow chart of a specific embodiment of the present invention.

FIG. 1 shows the experimental flow chart, cells in different groups are digested according to table 1. For each group, four wells of cells are digested. Count after digestion and freeze the cells, $1 \times 10^6$ of live cells per tube.

TABLE 1

| Study groups of the digestion solution on P2 cell | | |
|---|---|---|
| Group | Concentration of digestion solution | Digestion time |
| Experiment group 1 | 1 × TrypLE ™ + 0.5 mg/mL Dispase II digestion | 10 + 15 minutes |
| Experiment group 2 | 1 × TrypLE ™ + 2.0 mg/mL Dispase II digestion | 10 + 15 minutes |
| Experiment group 3 | 1 × TrypLE ™ + 10 mg/mL Dispase II digestion | 10 + 15 minutes |

Figure 2:
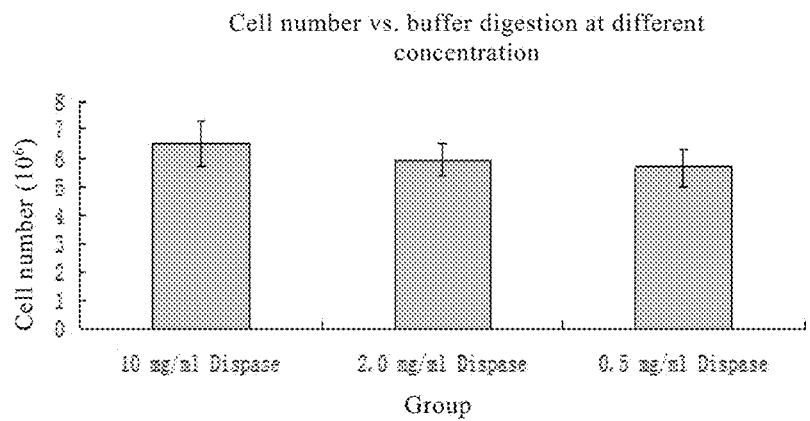
FIG. 2 shows the counting result after digestion with different concentrations of digestive enzymes.
Figure 3:
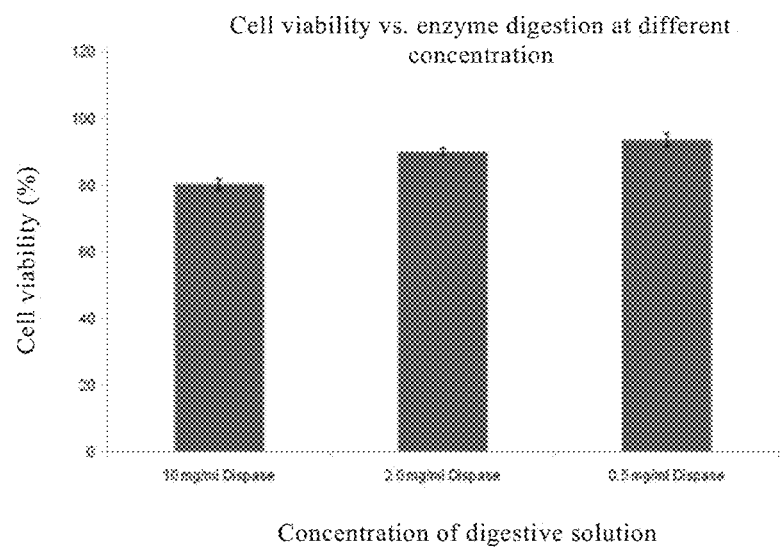
FIG. 3 shows the cell viability after digestion with different concentration of digestive enzymes.
Figure 4:
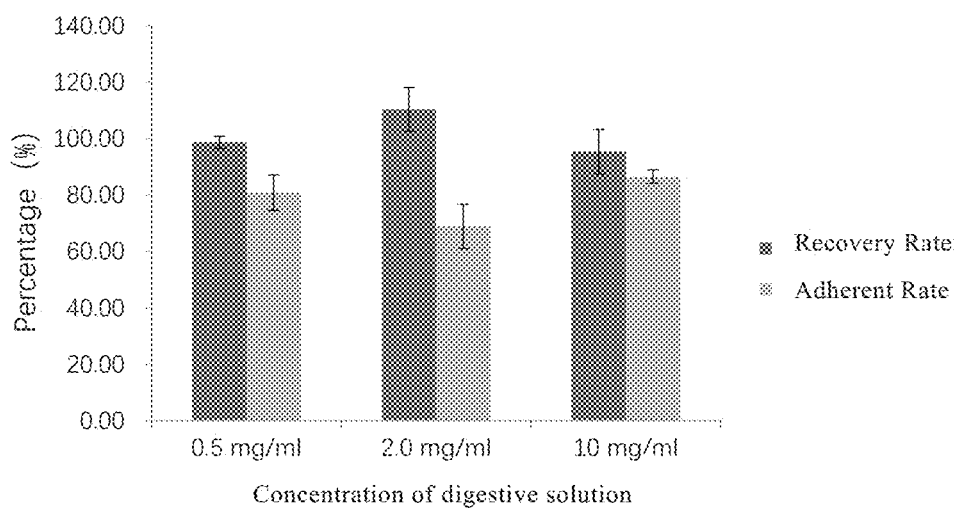
FIG. 4 shows the cell viability after digestion with different concentration of digestive enzymes.

As shown in FIGS. 2 to 4, the result shows that the cell viability after digestion with high concentration of digestive enzyme (10 mg/mL) is worse. The cell viability after digestion with low concentration of digestive enzyme (0.5 mg/mL) has no significant difference compared to that of the 2.0 mg/mL group, but it requires hard pipetting using pipetman to blow all the cells down. In sun, high-quality RPE cells can be obtained by Dispase II digestion at 2.0 mg/mL. However, the combination of 2.0 mg/mL Dispase II and 1×TrypLE™ is not conventionally selected randomly or simply. In fact, the inventor has found that RPE cells are characterized by a strong connection between cells, and even stronger connections between cells and substrate matrix. According to the characteristics of the two different connecting forces, the two-step digestion method of the inventor's invention finally determines the combination of 1×TrypLE™ and Dispase II after a large number of screening and experiments, and find that 2.0 mg/mL of Dispase II exerts the optimal effect.

Example 2: Comparison to Trypsin Combination

TrypLE™ select is purchased from Sigma, disperse enzyme Dispase II solution is purchased from ROCHE; RPE cells are from the P2 generation cells of primary dissociated human ocular tissue; DPBS is purchased from Sigma.

The adherent RPE cells are dissociated according to the steps:
(1) Pre-heating RPE complete medium, DPBS and TrypLE™ select in thermostat water bath at 37° C. for 5 to 10 minutes, and then transfer them into UV sanitized biosafety cabinet for use after sanitization by 75% ethanol.
(2) Obtaining the RPE cells cultured in 6-well plate for 10 days from $CO_2$ incubator to the biosafety cabinet, discarding the supernatant in 6-well plate, adding in 1 mL of DPBS and washing the cell surface twice.
(3) Discarding the abovementioned DPBS, adding in TrypLE™ select at 1.0 mL/well to cover well surface evenly, put it into $CO_2$ incubator at 37° C. for 10 minutes and discarding TrypLE™ select, and use trypsin for the control group; Discard the supernatant after wash the cell surface once with DPBS (calcium and magnesium free), adding in 1.0 mL of 2.0 mg/mL Dispase II solution diluted by DPBS (calcium and magnesium free), digesting in $CO_2$ incubator at 37° C. for 12 minutes.

(4) After digestion, discarding Dispase II solution, adding in 1 mL of RPE complete medium, aspirating the cells by gently pipetting gently, collecting the cells into 15 mL centrifugation tube and centrifuging at 2000 rpm for 5 minutes, discarding the supernatant, resuspending by DPBS and counting, freezing the cells according to the counting result, and getting them out from the liquid nitrogen tank to test the adherent rate afterwards.

Figure 5:
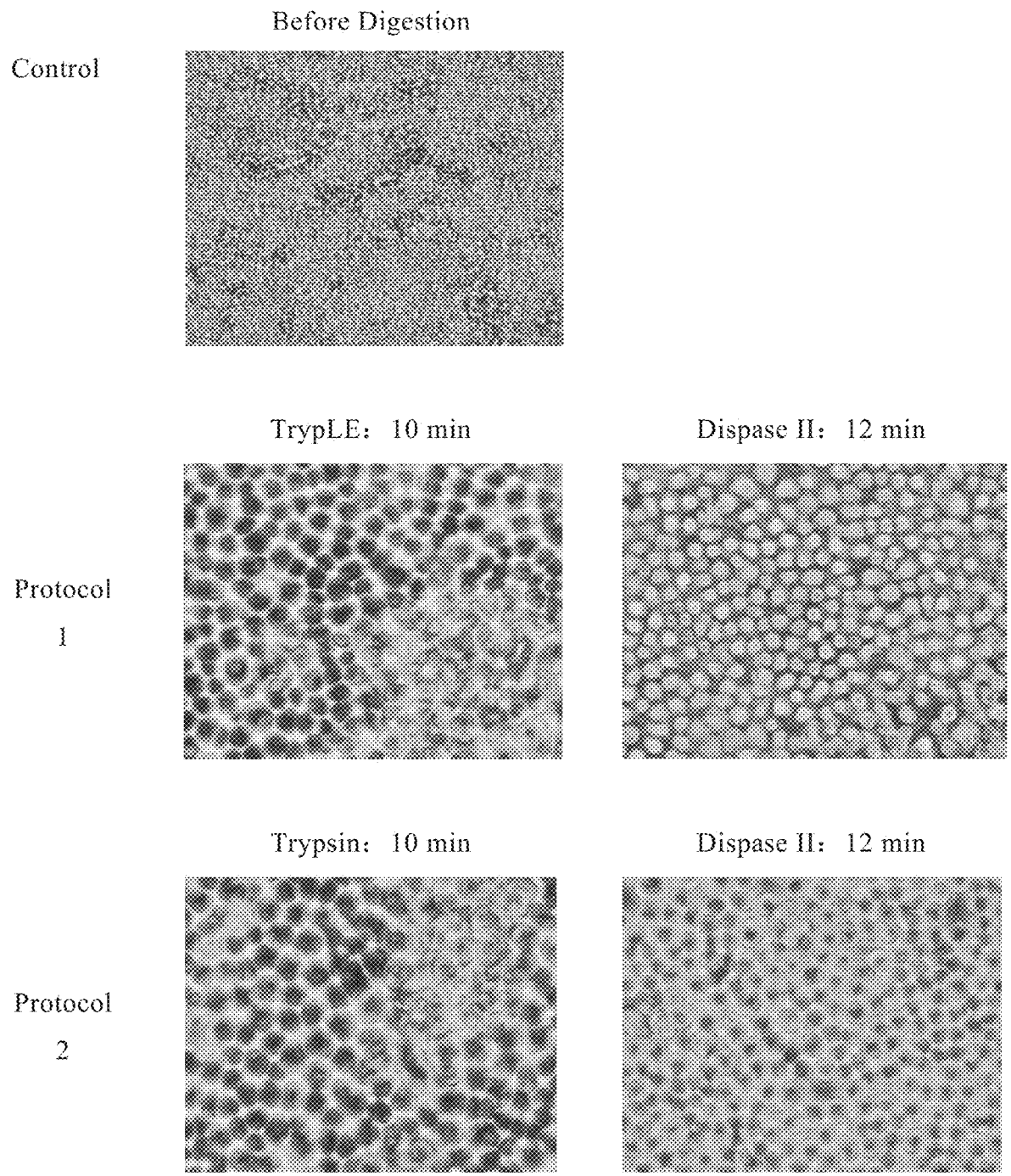
FIG. 5 shows the images of cells before or after digestion.
Figure 6:
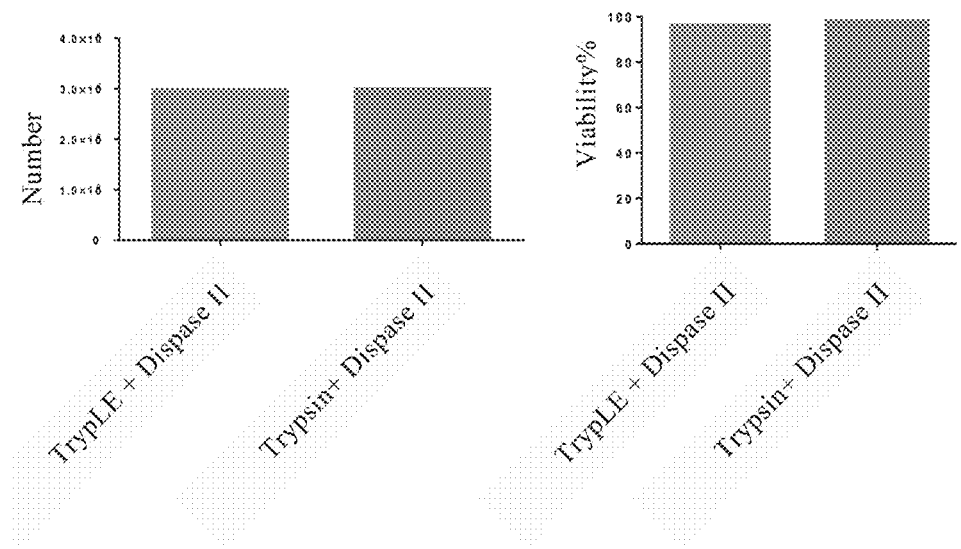
FIG. 6 shows the quantitation of cell number and cell viability after digestion with TrypLE™+Dispase II group and trypsin+Dispase II group, separately.
Figure 7:
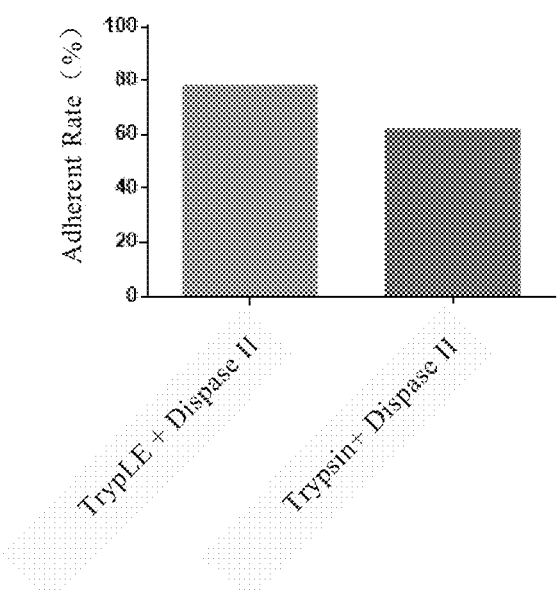
FIG. 7 shows the quantitation of cell adherent rate after TrypLE™+Dispase II group and trypsin+Dispase II group digestion, separately.

As shown in FIG. 5, the images of cells before and after trypsin digestion show that the effect of trypsin is not as good as that of TrypLE™, but generally equivalent. However, after adding in Dispase II solution again, the digestion effect of the TrypLE™ group is obviously better, showing the synergistic effect of TrypLE™ and Dispase II, i.e. in situation without affecting number and viability of RPE cells, the RPE cells have better disperse effect by the synergistic effect of TrypLE™ and Dispase II, and finally the cells have higher adherent ratio after freezing and recovery.

In fact, the inventor has found that the cell digestion way has a great influence on the adherent rate of cells after cryopreservation, however, there is no effective method to control cell adherence after cryopreservation and recovery in present techniques. The present invention has for the first time discovered the effect of digestion way on subsequent cell adherent rate for RPE cells, invented the two-step digestion method for RPE cells, and used TrypLE™ and Dispase II to greatly reduce the cost of culture and injection of RPE cells in clinic, and maintain the cell state and activity at a high level after recovery through the synergistic effect, which has good reproducibility.

Example 3: Digestion Effect by Using TrypLE™ or DispaseII Only

Figure 8:
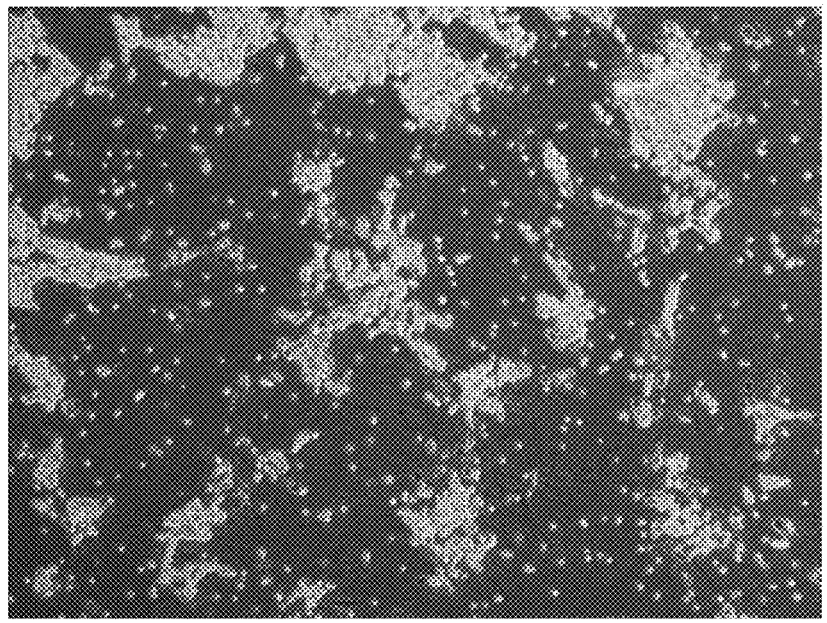
FIG. 8 shows the images of RPE cells after TrypLE™ digestion only.

When using a single enzyme such as TrypLE™ to digest cells, as it only works on cell-cell dissociation, it cannot achieve the expected digestion results; By experiments, it is found that cell dissociation time should be prolonged to more than 35 minutes, however, by that time part of the cells have already been damaged because of the over dissociation and will be lysed after pipetting, which resulting in cell number to be significantly lower than the actual number. Even though after hard pipetting, cells still cannot be dissociated from culture matrix completely, as shown specifically in FIG. 8. Therefore, the TrypLE™ digestion alone is not good.

Figure 9:
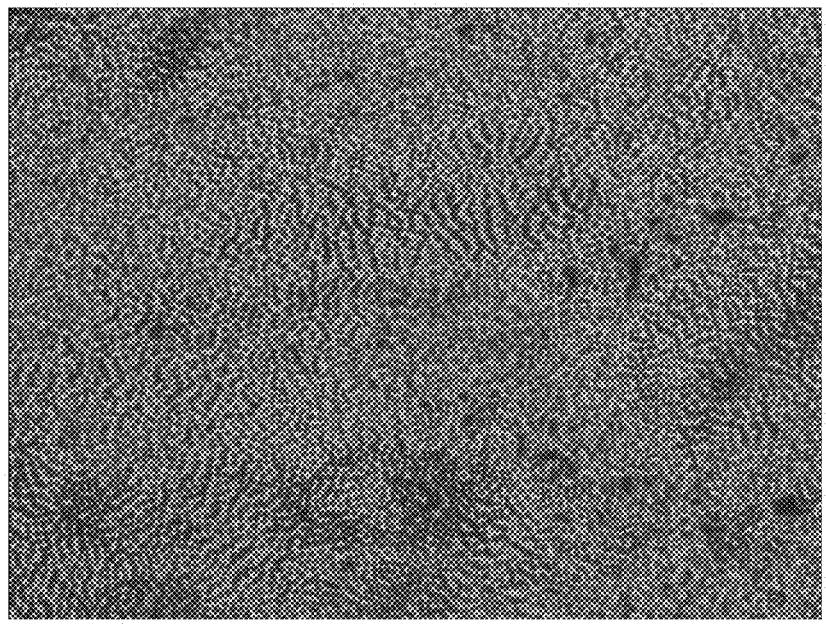
FIG. 9 shows the images of RPE cells after Dispase II digestion only.

As Dispase II is mild and found in the invention that it mainly functions on cell and culture matrix, dissociating cells by Dispase II alone can hardly dissociate cells, even after a very long time, as shown in FIG. 9 for dissociation effect.

Therefore, it further demonstrates that the RPE cells in Example 2 has much better disperse effect by the synergistic effect of TrypLE™ and Dispase II.

INCORPORATION BY REFERENCE

The entire disclosure of each of the patent documents and scientific articles referred to herein is incorporated by reference for all purposes

EQUIVALENTS

The invention may be embodied in other specific forms without departing from the essential characteristics thereof. The foregoing embodiments are therefore to be considered illustrative rather than limiting on the invention described herein. Scope of the invention is thus indicated by the appended claims rather than by the foregoing description, and all changes that come within the meaning and the range of equivalency of the claims are intended to be embraced therein.

The invention claimed is:

1. A method for digesting retinal pigment epithelium (RPE) cells to dissociate adherent RPE cells, comprising the steps of:
   (1) covering RPE cells evenly with a recombinant trypsin-like enzyme and incubating;
   (2) discarding the recombinant trypsin-like enzyme; and
   (3) covering RPE cells evenly with neutral protease Dispase II solution and incubating;
   wherein steps (1) to (3) are applied step by step; and
   wherein the concentration of the neutral protease Dispase II is from 0.5 mg/mL to 4.0 mg/mL.

2. The method of claim 1, wherein the RPE cells are cultured for about 10 to about 17 days.

3. The method of claim 1, wherein step (1) comprises incubating the RPE cells and the recombinant trypsin-like enzyme for about 14 to about 16 minutes at 37° C.

4. The method of claim 2, wherein step (3) comprises incubating the RPE cells and the neutral protease Dispase II for about 10 to about 15 minutes at 37° C.

5. The method of claim 1, wherein the RPE cells are cultured for over 17 days.

6. The method of claim 5, wherein step (3) comprises incubating the RPE cells and the neutral protease Dispase II for about 20 to about 22 minutes at 37° C.

7. The method of claim 1, further comprising washing the cells with calcium and magnesium free DPBS and discarding the DPBS before step (1) or step (3).

8. The method of claim 1, wherein the concentration of the neutral protease Dispase II is from about 2.0 mg/mL to about 4.0 mg/mL.

9. The method of claim 1, wherein the RPE cells are cultured for about 10 days or longer.

10. The method of claim 9, wherein step (3) comprises incubating the RPE cells and the neutral protease Dispase II for about 10 to about 15 minutes at 37° C.

* * * * *